US008372338B2

(12) United States Patent
Larsson

(10) Patent No.: US 8,372,338 B2
(45) Date of Patent: Feb. 12, 2013

(54) DEVICE AND METHOD FOR STERILIZING, COOLING, DRYING TRANSFERRING CLOSURES

(75) Inventor: Lars Joakim Larsson, Halmstad (SE)

(73) Assignee: Getinge Sterilization AB, Getinge (SE)

( * ) Notice: Subject to any disclaimer, the term of this patent is extended or adjusted under 35 U.S.C. 154(b) by 800 days.

(21) Appl. No.: 12/309,628

(22) PCT Filed: Aug. 11, 2007

(86) PCT No.: PCT/EP2007/007122
§ 371 (c)(1),
(2), (4) Date: Jan. 26, 2009

(87) PCT Pub. No.: WO2008/022723
PCT Pub. Date: Feb. 28, 2008

(65) Prior Publication Data
US 2009/0291019 A1 Nov. 26, 2009

(30) Foreign Application Priority Data
Aug. 23, 2006 (EP) ...................... 06119352

(51) Int. Cl.
A61L 2/08 (2006.01)
B08B 7/00 (2006.01)
B08B 9/00 (2006.01)
B08B 9/093 (2006.01)
B08B 9/20 (2006.01)
F16K 15/20 (2006.01)

(52) U.S. Cl. ................ 422/26; 422/1; 422/28; 422/568; 134/6; 134/22.12; 134/22.15; 134/22.18; 134/25.4; 137/15.01; 137/238

(58) Field of Classification Search ................ 422/1, 26, 422/28, 568, 302; 134/6, 22.12, 22.15, 22.18, 134/25.4; 137/15.01, 238
See application file for complete search history.

(56) References Cited

U.S. PATENT DOCUMENTS

| 4,385,035 | A | * | 5/1983 | Akitoshi et al. | ............. | 422/297 |
| 5,072,747 | A | * | 12/1991 | McCoy et al. | ................. | 134/48 |
| 5,901,718 | A | * | 5/1999 | Morimoto et al. | ........... | 134/120 |
| 6,659,115 | B1 | * | 12/2003 | Wieczorek | .................... | 134/120 |

FOREIGN PATENT DOCUMENTS

| DE | 27 39 169 | 3/1979 |
| DE | 28 01 568 | 7/1979 |

(Continued)

OTHER PUBLICATIONS

European Patent Office english translation of the description section of DE 2801568.*

(Continued)

Primary Examiner — Jill Warden
Assistant Examiner — Monzer Chorbaji
(74) Attorney, Agent, or Firm — Harness, Dickey & Pierce, P.L.C.

(57) ABSTRACT

The apparatus and method for sterilising caps/stoppers for pharmaceutical purposes comprises a vessel, pump, heater, circulation line. The sterilising liquid (hot water, steam) is heated and pumped to the vessel where a fluidised bed of caps etc. is generated. After leaving the vessel the liquid is circulated/heated. Optionally an additive (siliconisation in case rubber parts) or cooling liquid is added. Further, the vessel is disconnectably attached to the supply lines for transportation to a production facility.

10 Claims, 5 Drawing Sheets

FOREIGN PATENT DOCUMENTS

| | | | |
|---|---|---|---|
| DE | 2801568 | * | 7/1979 |
| DE | 32 48 555 | | 7/1984 |
| DE | 44 09 659 | | 9/1995 |
| DE | 44 09 659 A1 | * | 9/1995 |
| JP | 58-136143 U | | 9/1983 |
| WO | WO 00/61199 | | 10/2000 |

OTHER PUBLICATIONS

European Patent Office of the description seciton of DE 44 09 659 A1.*

Japanese Office Action dated Jul. 6, 2012 for corresponding Japanese Application No. 2009-524934.

* cited by examiner

DEVICE AND METHOD FOR STERILIZING, COOLING, DRYING TRANSFERRING CLOSURES

TECHNICAL AREA

The present invention relates to a multi-treatment sterilization device for sterilizing articles, such as closure elements, preferably for pharmaceutical purposes, which device comprises; a container adapted to perform multi-treatment of said articles being enclosed there within and a liquid transfer means to provide a liquid flow in said container. The present invention also relates to a method for sterilizing such articles.

BACKGROUND ART

Multi-treatment sterilization devices of the above type are well known in the art. Generally such devices are used to sterilize closures and caps, such as rubber stoppers for pharmaceutical containers and the like. The plurality of closures are subjected to several different treatments such as washing, sterilizing and drying in a multi-purpose container, wherein the closures being all in a heap in the container. Rubber stoppers are usually also siliconized, all within the same multi-purpose container. DE4409659 discloses an example of a cleaning and sterilizing installation.

After washing and siliconization but before steam sterilization, the closures are usually subjected to a pre-vacuum step in order to evacuate the presence of air and other unwanted fluids in the multi-purpose container. The un-evacuated air might have an isolating effect which may make the sterilization step more difficult and time consuming. During the sterilization treatment the multi-purpose container is supplied with heated steam until the closures have obtained sterilization temperature during an appropriate time.

The sterilized closures are usually subjected to an additional vacuum step before drying. The closures are dried with the supply of hot sterile air, for instance supplied in time intervals to the container. Subsequently the closures are subjected to a cooling treatment by cooled sterile air.

However, the sterilization may be troublesome for delicate closures, especially for some material compositions. The sterilization can create clumping of closures and in worst case the closures may be damaged due to the conditions in the multi-purpose container.

It is also desirable to reduce the process time in the multi-purpose container.

Finally it is advantageous to provide a robust, cost effective and reliable high quality multi-treatment sterilization device.

SUMMARY OF THE INVENTION

The object of the present invention is to provide a multi-treatment sterilization device and sterilization method which allows improvements in relation to prior-art sterilization devices in one or more of the above mentioned aspects.

In one aspect of the present invention, a sterilization device according to the introduction is further characterised in that said device is arranged to introduce liquid to said container to a predetermined level of said device, wherein said articles are at least partly submerged in liquid in said container during sterilization, said container comprises an inlet portion associated with said transfer means for providing said liquid flow and an outlet portion for receiving at least a part of said liquid flow, and wherein said liquid transfer means is adapted in such a way that said liquid flow is directed in a predetermined direction to reduce the contact forces between said articles.

By directing the liquid flow, the accumulated articles become more separated and distributed in said liquid which reduces the risk for clumping of articles. Thus, the liquid flow reduces the adhesive property, for instance for rubber stoppers in the multi-treatment container. The liquid flow also improves the sterilization effect of the liquid wherein articles being passed with admission liquid. Additionally the liquid in itself, in comparison of gas, may reduce the difference between the density of the article and fluid which may at least partly reduce the contact forces between the articles. The articles are effected in accordance with the principle of Archimedes. Thus, the relative weight of the articles may be reduced wherein the articles may be at least partly suspended in the liquid. The risk for damaging an article by the weight of the surrounding articles in the container are reduced. Additionally, sole gas treatment, such as a steam environment may further enlarge clumping difficulties for certain articles, such as articles becoming softer by an increased temperature.

The device according to the present invention also provides further advantages for associated multi-treatments, and achieves a gentle treatment of the articles in the process. For instance the sterilization may be performed without a prior pre-vacuum treatment. Additionally at least a part of the liquid used for sterilization may be added with silicon oil thereby improving the process both in time and effectiveness. In prior art devices, siliconized articles may be subjected to a final rinse, pre-vacuum treatment, steam sterilization or similar treatments after siliconization. However such treatments may reduce the silicon film on the siliconized article.

Further, heating treatment and cooling treatment may also be performed when the articles is submerged in liquid and optionally subjected to a fluid stream for separation and heat transfer purposes. Additionally such cooling treatment may be performed before drying treatment, thereby reducing adhesion and clumping risk of articles, wherein a lower temperature effectively may be enabled before drying is initiated.

The term "multi-treatment" may primary be referred to as at least one of the treatments; heating, sterilization, cooling and drying. Secondary multi-treatment may comprise at least one of the treatments washing, optionally rinsing, optionally siliconizing, sterilization and subsequent treatments, such as storing.

By the expression "articles", is meant delicate or fragile articles which have a tendency to be damaged. The term "damaged articles" may be clumped articles, or articles stuck together or subjected to abrasive wear. The articles or goods may be a product preferably sterilized in a heap, pile or similar way. The following are examples of an article; closure, stopper, plug, cap, for instance for pharmaceutical containers and delivery devices. In addition to pharmaceutical purposes, the articles may be used for other purposes where sterile products or purified products is desired, such as naturopathic preparations and lyophilized preparations.

The term "a predetermined level of said device" may for instance be that the container is at least partly introduced with liquid or that a fluid system of said device at least partly comprises liquid.

The term "at least partly submerged" is meant that an article may be at least partly surrounded by liquid and for instance a portion of an article may be facing the liquid surface exposing said portion. The articles may be separated by at least a liquid film.

The term "contact forces" is meant the contact forces of a certain duration, such as adhesion forces and preferably not relate to the instantaneous and momentary contact forces of articles, for instance during mutual impact. The liquid flow may be achieved by at least once applying a liquid stream in the predetermined direction.

The liquid transfer means is preferably adapted to move said articles by said liquid flow, at least initially, in a direction away from said inlet portion. Thus the articles may be separated effectively. The liquid flow may be adapted to the density difference of the article and the liquid for promoting fluidization of the articles.

The liquid transfer means may be adapted to achieve a state of essentially evenly distributed articles in the container liquid by said liquid flow. Thus, the flow may be adapted in relation to the density of said articles and liquid respectively, wherein the articles are essentially immovable, for instance seen in a vertical direction, in relation to the container. The container liquid preferably move relative the articles. Further, at least a share of all the articles may slightly move or swirl relative the container. The relative movement may for instance be a rotational or at least initially an essentially linear displacement.

The device preferably comprise a circulation passage, such as a by-pass passage, for circulating said liquid. The passage is preferably arranged externally said container enclosure defining an essentially closed system during at least a part of a treatment, such as a sterilization treatment. Alternatively the passage is arranged in said container, for instance defined by a partition wall.

The device may comprise a heating device for heating said liquid, preferably water to a predetermined sterilization temperature. Thus, the device may be adapted to perform a liquid heating sterilization. The liquid flow ensures a proper temperature distribution throughout the load of closures. The sterilization is preferably performed with superheated water with or without additive. The superheated water is essentially in liquid phase. Thus, the container being pressurised above atmospheric pressure, when using water as sterilization medium. The water may be one of; "water for injection" (WFI), distilled, purified and de-mineralised water or similar harmless and approved liquids. Alternatively, the flow in the container may be at least partly achieved by the heating device wherein the liquid in the container may have a segmented differing temperature which strive towards equalization in a liquid flow. In such a case, the liquid transfer means may be at least partly a heating device.

The device is advantageously arranged to sterilize an occurring liquid-absent space of said device, by gas, such as steam from the heated liquid, which space is facing a liquid surface of said device.

Thus conduit and other components of the device may be gas sterilized. The gas may be an additional supplied gas, preferably a sterilizing medium or at least a sterile gas. When using superheated water near a saturation point, steam may sterilize liquid-absent space. The space is preferably arranged above said predetermined level/surface.

The container is preferably adapted to be pressurized during sterilization, wherein said pressurization is at least partly due to said liquid heating. The pressurization may be due to additives or other partial pressures.

The device may comprises a bleeder valve to discharge surplus gases or the like. The valve may be arranged essentially at a top level in the fluid system of said device which communicates with said container. The valve or an additional valve may be adapted to discharge surplus liquids.

The device preferably comprise an additive supply unit, adapted to perform an additional treatment, such as a siliconization, after initiating sterilization of said articles. Thus, such a treatment may be at least partly integrated in a sterilization phase, such as in a preparation stage before sterilization which may reduce the process time. The additive may be supplied in association to the liquid supply which liquid are to be used at least partly during sterilization.

The device may comprise a cooling device wherein said articles being submerged in cooling liquid.

Thus, the cooling operation to a predetermined lower temperature, such as room temperature may be performed while the articles is being submerged in liquid (water). The liquid for cooling the articles may be at least a part of the liquid used during sterilization. By using the same liquid during cooling, the security in the system for using a sterile liquid is improved. The cooling operation may be performed before drying treatment wherein the articles may be less soft and having reduced clumping tendency.

The above objects, advantages and other aspects in relation to the device are also achieved by a method for sterilizing articles, such as closures, in a container adapted to perform multi-treatment of said articles being enclosed there within, comprising the steps of; introducing liquid to said container to essentially submerge said articles during sterilization, applying a liquid flow in a predetermined direction in said container by a liquid transfer means, wherein said liquid flow is directed in such a way that the contact forces are reduced between said articles.

The liquid flow may move said articles, at least initially, in a direction away from an inlet portion of said container.

The liquid flow may be adapted to at least partly movingly locate and evenly distribute said articles in an equilibrium state in the container liquid.

Thus the articles may be at least partly suspended in the liquid at an essential vertical location. The articles may be fluidized.

The method may comprise the step of circulating said liquid in a circulation passage.

The circulation passage may be the location wherein said liquid flow is generated, for instance by pumping.

The method may comprise the step of heating said liquid to a predetermined heating temperature, such as a sterilization temperature or a preparation temperature.

The method may comprise the step of pressurizing said container during sterilization, wherein said pressurization is at least partly due to said liquid heating. The pressurization may also depend on other pressurizations, such as an additive agents or gas.

The method may comprise the step of sterilizing an liquid-absent occurring space above a surface of said liquid by a sterilizing gas, such as steam emanating from said liquid.

The method may comprise the step of, siliconizing said articles which may be performed after initiating sterilization of said articles.

The term "after initiated" may be referred to wherein initial liquid needed for sterilization is introduced or prepared to be introduced.

The method may comprise the step of cooling said articles to a predetermined cooling temperature, wherein said articles being essentially submerged in cooling liquid. The cooling treatment may be achieved by a cooling device associated to the liquid system.

The method may comprise the steps of discharging said liquid out of said container, and depressurizing said container for further discharging. The depressurization may be at least a partial vacuum level or an essentially vacuum level. However the liquid may be discharged without such a vacuum step.

The method may comprise the step of supplying sterile gas to said liquid to agitate said articles in said container, for instance during a cooling treatment. If movements of the articles are desired, a sterile gas, such as sterile air may be introduced to the container. Such an agitation may be performed in an periodical manner during different treatments but preferably at least partly during cooling treatment and optionally during heating treatment, drying treatment and other treatments. Thus, the agitation is preferably non-mechanical.

The above objects may also be achieved by a multi-treatment sterilizing system according to another aspect of the present invention, which system, comprises a container adapted to perform multi-treatment of said articles, such as closures, being enclosed there within, at least one treatment station, a transport means and a transfer station for transferring said articles into a clean space for further processing such as packing, wherein said system is characterised in that said system comprises a multi-treatment sterilization device or the system being adapted to perform a method, in accordance with the above described device and methods, respectively.

The clean space may for instance be one of a filling machine, a bag, a bagging unit or similar arrangement.

BRIEF DESCRIPTION OF THE DRAWINGS

The invention will in the following be described with reference to the accompanying drawings, which for the purpose of exemplification illustrate a preferred embodiment of the invention.

DESCRIPTION OF PREFERRED EMBODIMENTS

Figure 1:
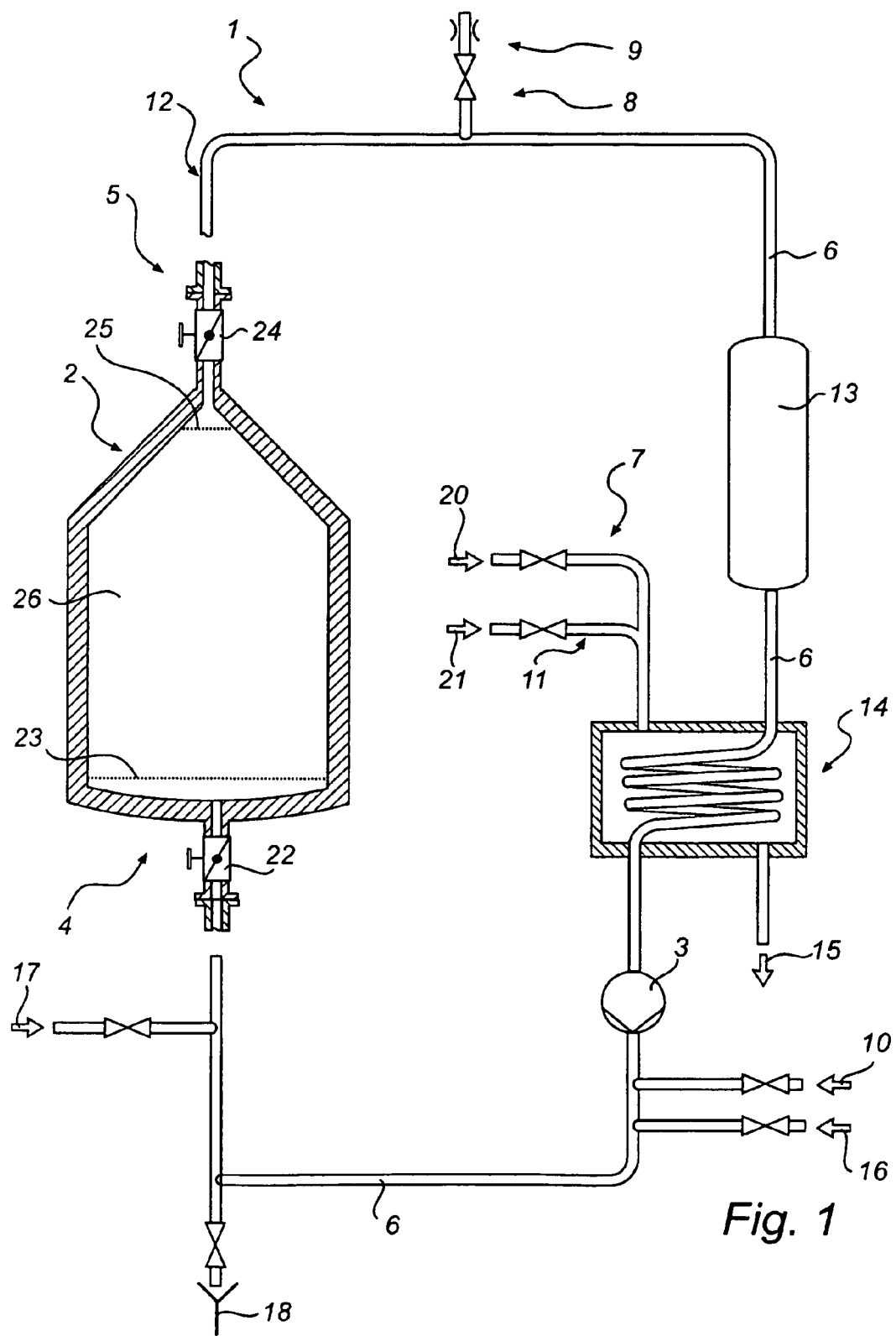
FIG. 1 is a schematic view of a sterilization device according to an embodiment of the invention.

FIG. 1 shows a sterilization device 1 according to a first embodiment of the invention, which has a multi-treatment container 2 which also is called a multi-purpose vessel. The vessel 2 is connectably arranged to a fluid system, such as a conduit system 12 for liquid as shown in FIG. 1. The fluid system 12 comprises a circulation passage 6 for circulating liquid in the fluid system. A valve, preferably a bleeder valve 9 is arranged in an upper portion, preferably the uppermost portion, of said fluid system in order to discharge surplus gases, such as air and steam.

According to this embodiment, the circulation conduit 6 is connected to a buffer, such as a buffer tank 13 for equalizing purposes. A heat exchanger 14 is arranged to change the temperature of the liquid. The heat exchanger 14 is controllably connected to a heating fluid source 20 forming part of a heating device 7. The exchanger 14 is also controllably connected to a cooling fluid source 21 forming part of a cooling device 11. The circulated liquid in the conduit system 12 is preferably separated from the cooling or heating flow. When the heating or cooling liquid has passed the exchanger such liquids may be discharged to a drain, such as a sewer 15. A liquid transfer means, such as a liquid pump 3 is arranged downstream the buffer tank 13 and the heat exchanger 14. The buffer tank 13 ensures that the liquid may be continuously brought to the pump and thereby reducing the risk of cavitation. Downstream the pump, the conduit system 12 is connected to an additive supply unit 10, which according to this embodiment may be a supply of silicon oil or the like for siliconizing treatment.

The process liquid used for sterilization is controllably introduced via supply inlet 16, which liquid may be water for injection (WFI) or other approved liquids. A sewer 18 for the process liquids is arranged below the vessel preferably upstream the vessel 2. Gas, such as sterile air or nitrogen gas, may be selectively supplied to the vessel via a gas supply unit 17.

The vessel is connectably arranged to a connection portion which according to this embodiment is a lower connection conduit 4 forming an inlet portion. The inlet portion has also an inlet valve 22. The vessel 2 comprises a lower liquid permeable section 23 preferably arranged adjacent the inlet portion. The upper part of the vessel is connectably arranged to a connection portion which according to this embodiment is an upper connection device 5 forming an outlet portion. The outlet portion has also an outlet valve 24.

The vessel 2 comprises an upper liquid permeable section 25, such as a net or a grid which preferably is arranged at the outlet portion. The section 25 may be arranged in the conduit 5 and is preferably detachably arranged. Alternatively the outlet portion may be arranged with a connection device in accordance with EP1196202 which connection device is being arranged at the vessel 2.

The interior peripheral walls of the vessel 2 and the lower and upper liquid permeable sections 23, 25 at least partly forms a treatment zone 26 for the articles to be treated and sterilized.

Figure 2A:
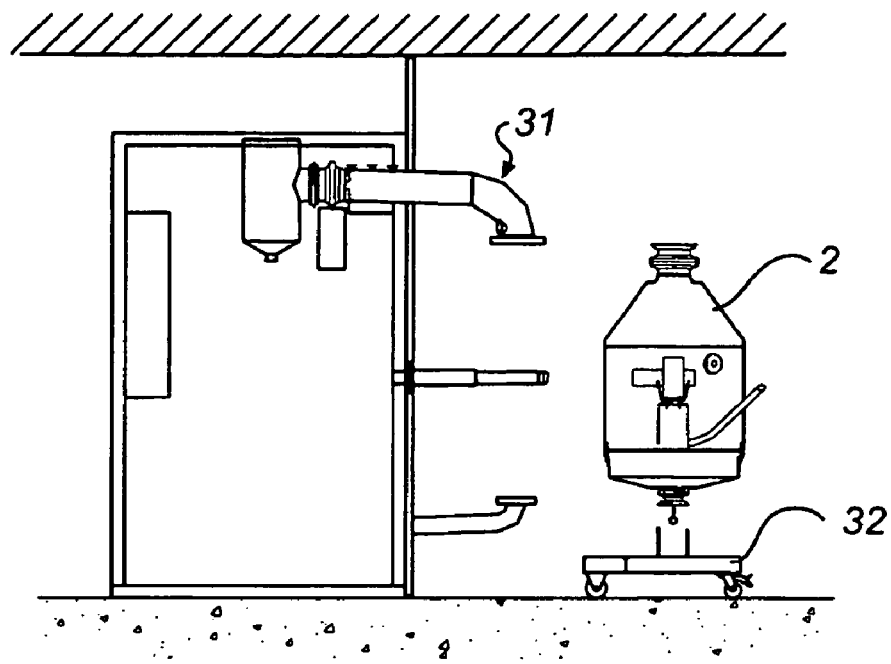
FIG. 2a schematically shows a part of a sterilization system comprising a sterilization device of FIG. 1.
Figure 2B:
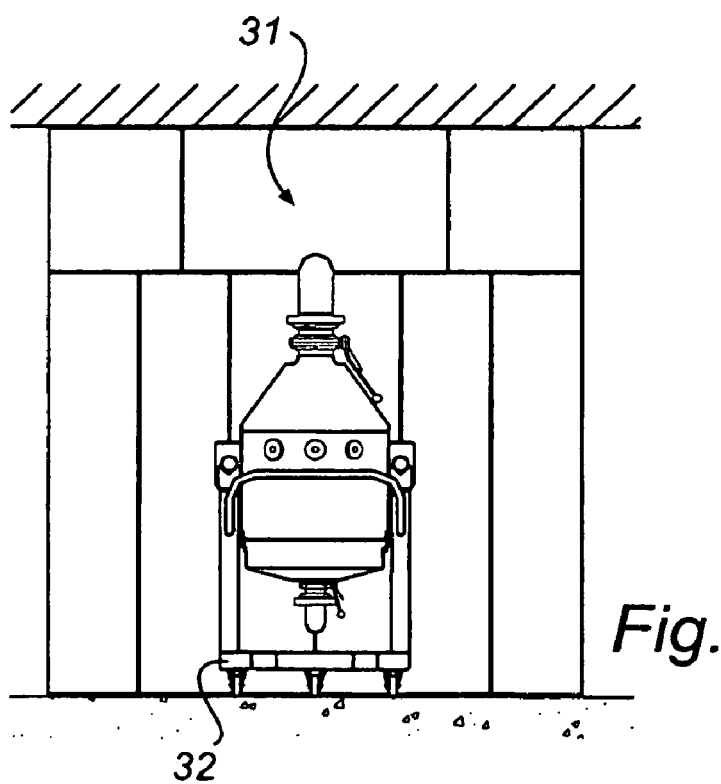
FIG. 2b shows the part of the sterilization system of FIG. 2a in a connected condition.

FIG. 2a shows the vessel which according to this embodiment is a mobile vessel 2. The vessel or the enclosure preferably have a volume between 50-1000 liter, more preferably between 50-500 liter and most preferred 50-400 liter. The vessel is supported by a trolley 32, which is partly depicted in FIG. 2a. The vessel may be docked to a treatment station 31 and which station is shown in FIG. 2b. The treatment station 31 is preferably adapted to perform multi-treatments, such as wash, siliconize, sterilize and dry. The treatments may specifically be detergent wash, rinsing, optionally pre-vacuum, liquid filling, siliconizing, heating, sterilization, cooling, emptying and drying.

Figure 3:
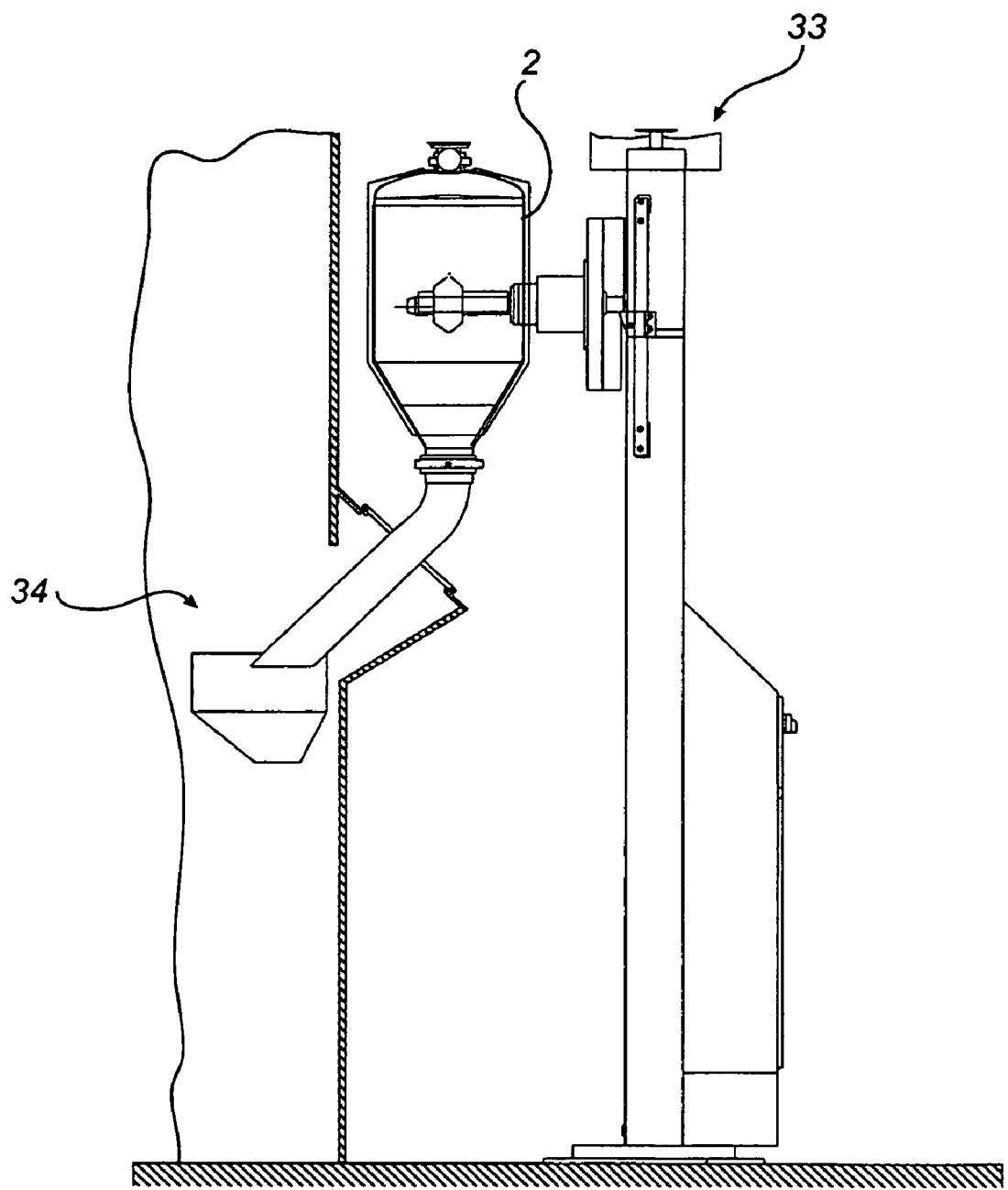
FIG. 3 shows an additional part of the sterilization system.

FIG. 3 shows a transfer station in the form of a lift and turn station 33 for transferring treated articles into a clean area for further processing such as packing. In this embodiment the vessel 2 is connected to a filling machine 34 to discharge the articles aseptically. Alternatively the articles may be directly transferred to a filling line for packing after treatments of the articles. For instance the vessel may comprise a connection device in accordance with EP1196202. Thus, the sterilization system enables a complete unbroken aseptic chain comprising treatment at the treatment station, storage in the vessel, distribution and transfer of the articles.

Figure 4:
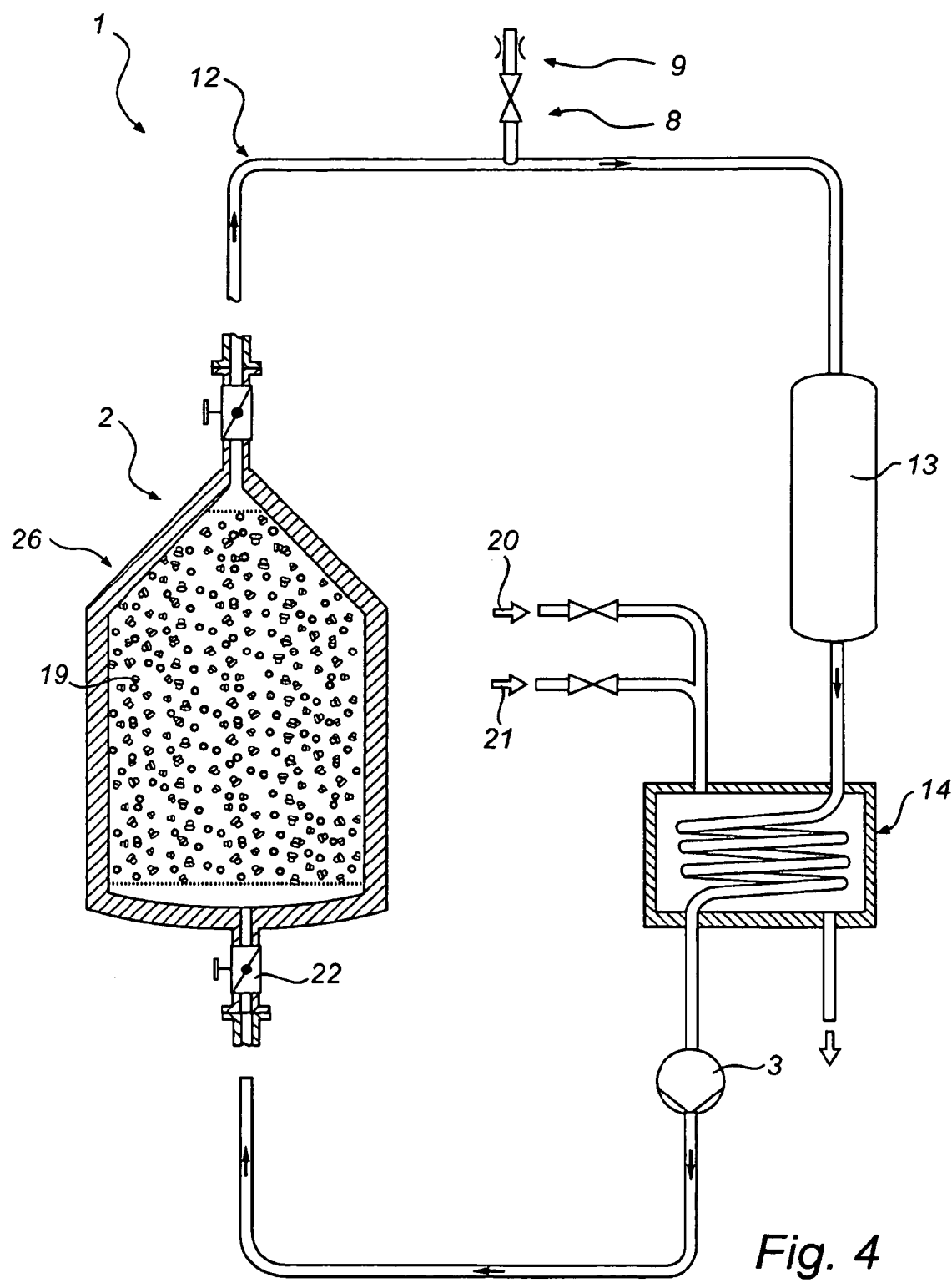
FIG. 4 schematically shows a treatment in the sterilization device shown in FIG. 1.

FIG. 4 shows the sterilization device 1 during liquid treatment, such as during heating and sterilization. The load in the form of articles 19 are loaded into the vessel 2. The articles used may be closures of a delicate and adhesion sensitive material which may have a risk for agglomeration. The article materials may be one of a polymer material, synthetic or natural rubber. Non limiting examples of other articles may be crimp caps, agitation beads, combi-seals and aluminium caps.

The articles may be troublesome in other aspects as for instance a material composition or density having a risk for agglomeration, especially articles having a density higher than the liquid used in the fluid system 12. Other delicate issues may be that the articles may be sensitive to abrasive wear. For instance the liquid treatment may be more lenient than forceful gas mixing and wherein non-mechanical agitation can be avoided.

After appropriate treatments such as washing and rinsing, liquid is introduced to the vessel forming a liquid surface so that the articles are essentially covered by liquid. For instance, if the articles have cavities, especially deep cavities, a pre-vacuum treatment may selectively be performed before liquid is introduced. The liquid may be introduced from the supply inlet 16 or the buffer tank 13.

The liquid submersion at least partly reduces the contact forces between the articles. The contact forces are more reduced in contrast to a gas filled vessel.

With reference to FIG. 4, the liquid is preferably circulated in an essentially closed system which system is essentially closed or one-way directed at least during sterilization. However, the bleeder valve 9 may be opened in a one way direction out of said system 12 at least during a part of the sterilization time or heating time. The discharging of air and other surplus gases is important for achieving a proper sterilization. The fluid system 12 may comprise liquid-absent spaces 8, for instance adjacent the bleeder valve 9.

The arrows indicates the preferred flow in the liquid system 12. The circulation in the system 12 ensures a proper temperature distribution in the treatment zone 26. The direction and intensity of the flow is adapted to the tendency to agglomerate and the density of the articles for distributing and allocating the articles in the treatment zone 26 that is filled with liquid. The articles are preferably movingly located between the lower and upper liquid permeable section. Thus the contact forces emanating from gravity may additionally be reduced by the flow. Thereby may the risk for agglomerated articles be reduced.

The vessel preferably comprise at least a part of the same liquid used during heating as well as during sterilization. Occurring surplus of gas and liquid may for instance be discharged via the bleeding valve 9. At least a part of that water used may also be used in the cooling phase. Thus the articles may be siliconized at a later stage than in prior art devices, for instance in association to the heating treatment or later. The temperature of the liquid may be regulated by the exchanger 14 by means of the heating fluid 20 and cooling fluid 21. The temperature in the vessel when heating treatment is initiated may be approximately 110° C., wherein the vessel being pressurized. According to this embodiment the sterilization temperature is preferably above 120° C., more preferred 120-137° C. and most preferred 120-125° C. The pressure above atmospheric is preferably above 1 bar during sterilization and may be near or approximately at a saturation point. Thus, occurring liquid absent space above the liquid surface, including associated conduits and other components may be sterilized by sterilizing gas such as steam.

It should be noted that other temperatures and pressures may be considered by a person skilled in the art, especially if other liquids and agents are used.

Figure 5:
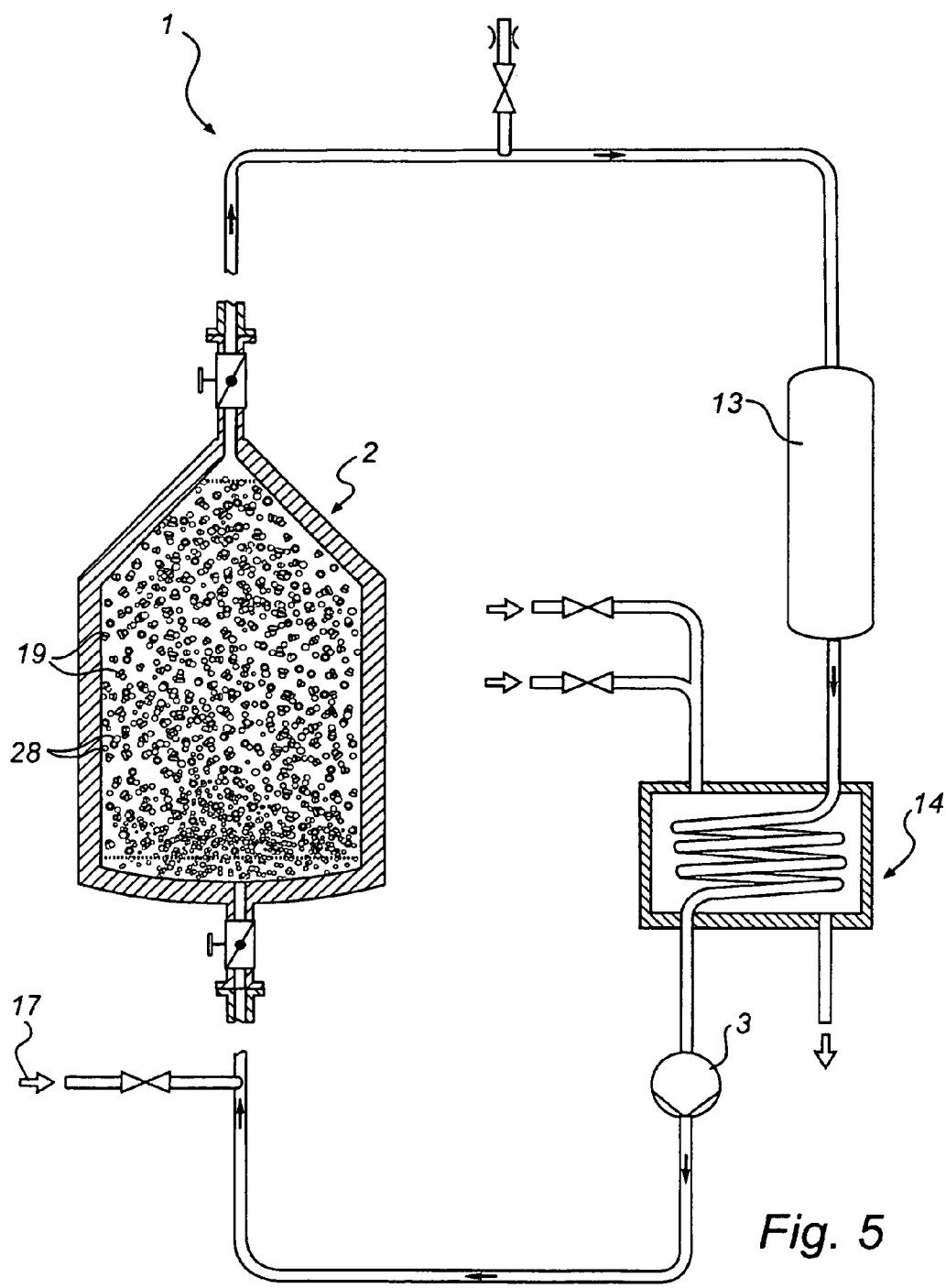
FIG. 5 schematically shows an additional treatment in the sterilization device shown in FIG. 1.

FIG. 5 shows an additional treatment when the articles are submerged in liquid and being agitated with a gas flow. Such treatment may be performed when desired during different treatments, such as the heating and cooling treatments. Preferably is such a treatment avoided during sterilization as the gas may reduce the sterilizing effect.

The gas is preferably sterile air and may be supplied from the gas supply unit 17 as shown in FIG. 1. The gas is depicted as air bubbles 28 in FIG. 5. The gas may be continuously or pulsatingly supplied for homogenous mixing of articles. Apart from the preferred liquid circulation, the additional agitation may also accelerate the treatment in progress, such as washing, rinsing, siliconizing, heating and cooling treatment.

It will be appreciated that the above-described embodiment of the invention can be modified and varied by a person skilled in the art without departing from the inventive concept defined in the claims. For instance the container may comprise several outlets or outlet portions, wherein one may be selected. Such a selection may depend on the present load and amount of articles or other process parameters for achieving an appropriate circulation or process optimization.

Additionally an opposite direction may be used, for instance if the density of the articles is lower than the liquid density. Also the density of the articles may be adapted to be essentially similar as the density of the liquid used during sterilization or vice versa.

Further, the vessel or other machine components may be rotatingly arranged for selected mixing of the articles.

Also, the flow may be pulsating for moving the articles in the vessel for reducing the risk of agglomeration.

According to another aspect of the present invention, the sterilization may be performed in a sterilization chamber being of a similar kind as an autoclave chamber, preferably using super heated water essentially in liquid phase.

The invention claimed is:

1. A method for sterilizing articles in a container adapted to perform multi-treatment of said articles being enclosed there within, comprising:
   introducing water, with or without additive, into said container to submerge said articles during sterilization;
   heating said water, with or without additive, under pressure, above atmospheric pressure, to a sterilization temperature; and
   applying a liquid flow of said water, with or without additive, from an inlet portion to an outlet portion of said container, said outlet portion being arranged at a higher vertical position than said inlet portion by a liquid transfer means, wherein said liquid flow is directed in such a way that the contact forces are reduced between said articles.

2. The method according to claim 1, further comprising:
   circulating said water, with or without additive, in a circulation passage.

3. The method of according to claim 1, further comprising:
   sterilizing a liquid-absent occurring space above a surface of said water, with or without additive, by a sterilizing gas.

4. The method according to claim 1, further comprising:
   siliconizing said articles after initiating sterilization of said articles.

5. The method according to claim 1, further comprising:
   cooling said articles to a cooling temperature, wherein said articles being essentially submerged in cooling liquid.

6. The method according to claim 5, further comprising:
   discharging said water, with or without additive, out of said container, and
   depressurizing said container for further discharging.

7. The method according to claim 1, further comprising:
   supplying sterile gas to said water, with or without additive, to agitate said articles in said container.

8. The method according to claim 1, wherein the sterilization temperature is above 120° C.

9. A method for multi-treatment of articles in a container adapted to perform multi-treatment of the articles being enclosed therein, comprising:
 washing and rinsing the articles; and
 sterilizing the articles, wherein the sterilizing comprises:
  introducing water, with or without additive, to the container to submerge the articles during sterilization;
  heating the water, with or without additive, under pressure, above atmospheric pressure, to a sterilization'temperature; and
  applying a liquid flow of superheated water through the container from an inlet to an outlet thereof, said outlet being arranged at a higher vertical position than said inlet.

10. The method according to claim 9, wherein the sterilization temperature is above 120° C.

* * * * *